United States Patent [19]

Tsuchida et al.

[11] Patent Number: 4,588,687

[45] Date of Patent: May 13, 1986

[54] METHOD FOR PRODUCING L-TRYPTOPHAN BY FERMENTATION

[75] Inventors: Takayasu Tsuchida, Yokohama; Osamu Kurahashi; Hiroki Kawashima, both of Kawasaki; Shigeru Nakamori, Yokohama; Hitoshi Enei, Zushi, all of Japan

[73] Assignee: Ajinomoto Company Incorporated, Tokyo, Japan

[21] Appl. No.: 444,151

[22] Filed: Nov. 24, 1982

[30] Foreign Application Priority Data

Nov. 24, 1981 [JP] Japan ................................ 56-188089

[51] Int. Cl.[4] ...................... C12P 13/22; C12N 15/00; C12N 1/20; C12N 1/00

[52] U.S. Cl. ................................ 435/108; 435/172.3; 435/253; 435/317

[58] Field of Search ..................... 435/108, 172.2, 253, 435/317

[56] References Cited

U.S. PATENT DOCUMENTS

| | | | |
|---|---|---|---|
| 4,302,544 | 11/1981 | Young et al. | 435/253 |
| 4,363,875 | 12/1982 | Akashiba et al. | 435/839 |
| 4,371,614 | 2/1983 | Anderson et al. | 435/68 |
| 4,430,434 | 2/1984 | Sanders et al. | 435/68 |

FOREIGN PATENT DOCUMENTS

| | | | |
|---|---|---|---|
| 0071397 | 5/1982 | Japan | 435/847 |
| 0208994 | 12/1982 | Japan | 435/108 |
| 2078731 | 1/1982 | United Kingdom | 435/108 |

OTHER PUBLICATIONS

*Chemical Abstracts*, vol. 95, p. 339, (1981), Abstract No. 57898q: Okunev, O. V. et al, "Obtaining Hybrid Plasmids Containing *Bacillus subtilis* Genes".

Keggins et al, *Proc. Natl. Acad. Sci.*, vol. 75, No. 3, pp. 1423–1427 (1978), "Molecular Cloning of Genetically Active Fragments of Bacillus DNA in *Bacillus subtilis* and Properties of the Vector Plasmid pUB110".

*Methods in Enzymology*, vol. 68, Recombinant DNA; Wu, R. ed., Academic Press, New York, pp. 342–357 (1979).

*Primary Examiner*—Thomas G. Wiseman
*Assistant Examiner*—Robin Lyn Teskin
*Attorney, Agent, or Firm*—Oblon, Fisher, Spivak, McClelland & Maier

[57] ABSTRACT

A method for producing L-tryptophan by fermentation in high yields employing a microorganism of the genus Bacillus, which has been constructed by a gene splicing technique by incorporating a recombinant plasmid DNA containing an inserted DNA containing fragment controlling resistance to tryptophan-antagonists into a recipient strain of the genus Bacillus. The incorporated DNA fragment is a mutant of the genus Bacillus which was obtained from resistant to tryptophan-antagonists.

2 Claims, No Drawings

METHOD FOR PRODUCING L-TRYPTOPHAN BY FERMENTATION

BACKGROUND OF THE INVENTION

1. Field of the Invention

The present invention relates to a method for producing L-tryptophan by fermentation, and particularly relates to a method for producing L-tryptophan with a microorganism of the genus Bacillus constructed by a gene splicing technique.

2. Description of the Prior Art

There have been two processes for the production of L-tryptophan by microbiological process: one is an enzymological process using indole and serine (or pyruvic acid and ammonia) as the starting materials and another is a feremention process using carbohydrate as the carbon source, in which anthranilic acid or indole is sometimes used as an additional carbon source. The present invention concerns the latter fermentation process.

Examples of known microorganisms which produce L-tryptophan from carbohydrate through a fermentation process are a mutant of the genus Brevibacterium resistant to 5-methyltryptophan (U.S. Pat. No. 3,700,539), a mutant of Corynebacterium resistant to tryptophan-analog and phenylalanine-analog and requiring phenylalanine and tyrosine for growth (U.S. Pat. No. 3,849,251), a mutant of Bacillus resistant to 5-fluorotryptophan and requiring arginine, phenylalanine, lysine, leucine, or purine for growth (Japanese Published Examined patent application No. 39517/1978), a mutant of Bacillus resistant to 5-fluorotryptophan (Japanese Published Unexamined patent application No. 148093/1976), and a mutant of Enterobacter (Japanese Published Unexamined patent application No. 57888/1976).

Examples of known microorganisms which produce L-tryptophan from carbohydrate and anthranilic acid through a fermentation process are a wild strain of Aerobacter, Arthrobacter, Bacillus, Brevibacterium, Staphylococcus, Corynebacterium, Flavobacterium, Pseudomonas, Proteus, Serratia, Sarcina, Streptococcus, Xanthomonas, Candida, Saccharamyces, Zygosaccharomyces or Penicillium (Japanese Published Examined patent application No. 20711/1968), a mutant of Bacillus resistant to anthranilic acid and requiring anthranilic acid for growth (Japanese Published Examined patent application No. 29584/1972), a wild strain of Escherichia (French Pat. No. 1,207,437) and a mutant of Bacillus resistant to 5-methyltryptophan (British Pat. No. 1,298,499).

Examples of known microorganisms which produce L-tryptophan from carbohydrate and indole through a fermentation process are a wild strain of Candida (British Pat. No. 1,222,904), a mutant of Escherichia requiring anthranilic acid (U.S. Pat. No. 3,293,141), and a wild strain of Bacillus (U.S. Pat. No. 3,700,558).

Other examples of known microorganisms which produce L-tryptophan from carbohydrate are those which were constructed by gene splicing technique and are *Escherichia coli* strains having recombinant plasmid DNA disclosed in Japanese Published Unexamined patent applications No. 71397/1982 and No. 80398/1982, and Appl. Environ. Microbiol.,38, (2), 181–190, (1979).

However, it has been difficult to apply the known methods to commercial production of L-tryptophan because of the rather low L-tryptophan productivity of the known microorganisms.

A need therefore continues to exist for development of a novel process for production of L-tryptophan in high yields.

SUMMARY OF THE INVENTION

It is therefore an object of the present invention to provide for a novel method for producing L-tryptophan by fermentation in high yields. This and other objects of the invention has been attained by providing a method for producing L-tryptophan by fermentation which comprises aerobically culturing an L-tryptophan producing microorganism in an aqueous culture medium, and recovering the L-tryptophan accumulated in the aqueous culture medium; said L-tryptophan producing microorganism having been constructed by incorporating a recombinant plasmid DNA inserted with a DNA fragment controlling resistance to a tryptophan-antagonist, obtained from a chromosomal DNA of a mutant of the genus Bacillus resistant to said tryptophan-antagonist, into a recipient strain of the genus Bacillus.

DETAILED DESCRIPTION OF THE PREFERRED EMBODIMENTS

The tryptophan-antagonist of the present invention inhibits the growth of microorganisms of the genus Bacillus, but the inhibition is suppressed partly or completely when L-tryptophan coexists in the medium.

Examples of tryptophan-antagonists are 4-fluorotryptophan, 5-fluorotryptophan, 6-fluorotryptophan, 7-fluorotryptophan, 4-methyltryptophan, 5-methyltryptophan, 6-methyltryptophan, 7-methyltryptophan, naphtylalanine, indorylacrylic acid, naphtylacrylic acid, $\beta$-(2-benzothienyl)-alanine, styrylacetic acid and tryptazan.

Although any mutants of the genus Bacillus resistant to tryptophan-antagonist can be used as the DNA-donors, mutants having high resistance are preferred. In many cases, better results can be obtained when mutants having higher productivity of L-tryptophan are used as the DNA-donor. The mutant resistant to tryptophanantogonist can be obtained by conventional mutation techniques such as exposing parent of the genus Bacillus to 250 $\mu$g/ml of N-methyl-N'-nitro-N-nitrosoguanidine in a buffer solution and separating the colonies which appear on the agar medium containing an amount of tryptophan-antagonist inhibitive to the growth of the parent strain. Such DNA-donors naturally have a chromosomal DNA region controlling resistance to tryptophan-antagonist.

Extraction of chromosomal DNA can be carried out by a conventional manner as described in Bacteriol, 89, 1065, (1965).

As the vector DNA, plasmid DNAs which propagate in hosts of Bacillus are used. Typical vector DNAs are pCT 127, pc 194, pC 221, pC 223 and pUB 112 (Proc. Natl. Acad. Sci. U.S.A., 74, 1680–1682 (1977)), pUB 110 (J. Bacteriol., 134, 318–329 (1978), and pTP 4 and pTP 5 (Microbiol Letters, 5, 55–59 (1978)), all of which are derived from plasmids of Staphylococcus, and pLS 15 and pLS 28 (J. Bacteriol., 131, 699–701 (1977)), pLS 13 (J. Bacteriol., 129, 1487–1494 (1977)), and pPL, pPL 2 (J. Bacteriol 124, 484 (1975), all of which are derived from plasmids of Bacillus.

The chromosomal DNA is digested with a restriction endonuclease by a well known method (Biochem. Biophys. Acta, 383, 457, (1975)). Various kind of restriction endonucleases can be used if the degree of digestion is controlled by changing reaction time. The vector DNA is also cleaved with a restriction endonuclease. Suitable restriction endonuclease for each vector DNA is disclosed in the literature shown in parenthesis above.

Recombination of DNA to prepare the recombinant plasmid can be carried out by a ligation reaction with a ligase, or by incorporating with terminal transferase deoxyadenylic acid and thymidylic acid, or deoxyguanylic acid and deoxycytidylic acid into the chromosomal DNA fragment and cleaved vector DNA and by subjecting the modified chromosmal DNA fragment and cleaved DNA to an annealing reaction.

The recombinant DNA thus obtained can be incorporated into the DNA-recipient by treating the cell of the DNA-recipient with calcium chloride to increase the permeability as is reported regarding *E. coli* K-12 (Mandel, M. and Higa, A., J. Mol. Biol., 53, 159 (1970)), or by applying to the incorporating cells of the DNA-recipient at a specific stage of growth when the cells become capable of incorporating plasmids (competent cell) as is reported in *Bacillus subtilis* (Duncan, C. H., Wilson, G. A. and Young, F. E., Gene 1, 153 (1977)). The recombinant DNA can also be incorporated into the DNA-recipient by forming protoplast or spheroplast of the DNA-recipient which easily incorporates plasmid DNA as is known in *Bacillus subtilis*, actinomycetes and yeast (Chang, S. and Choen, S.N., Molec, Gen. Genet, 168, 111 (1979)); Bibb, M. J. Ward, J. M. and Hopwood, O. A., Nature, 274, 398 (1978); Hinnen, A., Hicks, J. B. and Fink, G. R., Proc. Natl, Acad. Sci., USA, 75, 1929 (1978)).

The recipient for the recombinant DNA are microorganisms of the genus Bacillus. It is convenient to use, as the DNA recipient, microorganisms sensitive to tryptophan-analogue and requiring tryptophan for growth for the selection of transformant having a recombinant DNA inserted with chromosomal DNA fragment controlling resistance to tryptophan-antagonist. When the recombinant plasmid DNA inserted with chromosomal DNA fragment controlling resistance to tryptophan-antagonist is used for transformation after selection of the recombinant plasmid DNA using a host sensitive to tryptophan-antagonist and requiring L-tryptophan for growth, microorganisms resistant to tryptophan-antagonist and having no requirement of L-tryptophan for growth can be used as the DNA recipient.

The desired transformants are those which become resistant to tryptophan-antagonist and are capable of producing L-tryptophan in case microorganisms sensitive to tryptophan-antagonist and requiring L-tryptophan for growth are used as the recipients. In case microorganisms resistant to tryptophan-antagonist and having no requirement of L-tryptophan for growth are used, the desired transformants are those which have the characteristics possessed by the vector DNA as the maker for selection.

The methods of cultivation of the L-tryptophan producing transformants thus obtained are conventional, and are similar to the methods for the cultivation of known L-tryptophan producing microorganisms. The aqueous culture medium employed is a conventional one containing carbon source, nitrogen source, inorganic ions and, when required, minor organic nutrients such as vitamins and amino acids.

As for the carbon source, carbohydrate such as glucose, sucrose, lactose, fructose and raw material containing such saccharide (such as starch hydrolysate, molasses and fruit juice) is used. Together with the carbohydrate, an intermediate compound for the production of L-tryptophan, such as anthranilic acid on indole, can be used as the carbon source. The concentration of the intermediate compound in the medium is maintained at a low level, when it is used, to avoid inhibition of the growth of the transformant. Gaseous ammonia, aqueous ammonia, ammonium salts and other nitrogen containing materials can be used as the nitrogen source.

Cultivation of the tryptophan is conducted under aerobic conditions in which the pH and the temperature of the aqueous culture medium are adjusted to a suitable level previously determined and continued until production of L-tryptophan ceases.

EXAMPLE 1

(1) Extraction of chromosomal DNA

Bacillus subtilis AJ 11713 (FERM-BP 208) requiring L-arginine and L-leucine and resistant to 5-fluorotryptophan was cultured in 1 l of "Bact Penassay Broth" (Difco) at 30° C. for 2 hours with shaking, and cells in exponential growth phase were harvested. Chromosomal DNA extracted from the cells by a conventional phenol-method, and 4.1 mg of purified DNA was obtained.

(2) Insertion of chromosomal DNA fragment into vector

As the vector, pUB 110 possessing genetic information of kanamycin-resistance and neomycin-resistance was used.

Ten μg of the chromosomal DNA obtained in step (1 ) and 5 μg of vector DNA were digested separately with endonuclease Eco RI at 37° C. for 1 hour, and thereafter the two reaction mixtures were heated at 65° C. for 10 minutes and mixed. The mixed solution was subjected to ligation reaction by a $T_4$ phage DNA-ligase in the presence of ATP and dithreitol at 10° C. for 24 hours.

(3) Genetic transformation with the plasmid having tryptophan producing gene.

*Bacillus subtilis* AJ 11712 which requires L-arginine, L-leucine and L-tryptophan was cultured in "Penassay Broth" (Difco) at 30° C. overnight with shaking, and thereafter culturing at 37° C. for 4 hours with shaking in Medium-I (containing 0.5 g/dl glucose, 0.2 g/dl $(NH_4)_2SO_4$, 0.6 g/dl $KH_2HPO_4$, 0.02 g/dl $MgSO_4$. $7H_20$, 0.1 g/dl sodium citrate, 0.2 g/dl yeast extract, 10 mg/dl L-tryptophan, 25 mg/dl L-arginine and 5 mg/dl L-leucine), and further cultured, after the cultivation in Medium-I, at 37° C. for 1.5 hours with shaking in Medium-II (containing 0.5 g/dl glucose, 0.2 g/dl $(NH_4)_2SO_4$, 0.6 g/dl $KH_2PO_4$, 1.4 g/dl $K_2HPO_4$, 0.12 g/dl $MgSO_4.7H_2O$, 0.1 g/dl sodium citrate 0.02 g/dl yeast extract, 5 mg/dl L-arginine and 0.5 mg/dl L-leucine). Thus, competent cells having the ability of plasmid uptake were obtained. (C. Anagnostopoulos J. Spizizen: J. Bacteriol, 81, 741, (1961)).

A suspension of the competent cells was added with the hybrid plasmid having tryptophan producing gene obtained in step (2), and incubated at 37° C. for 2 hours with shaking to complete the transformation reaction.

The cell-suspension was transferred onto a minimum medium prepared by adding 5 μg/ml kanamycin, 10 mg/dl L-leucine, 10 mg/dl L-arginine and 2 g/dl agar to a basal minimum medium of pH 7.2 containing 0.6 g/dl $KH_2PO_4$, 1.4 g/dl $K_2HPO_4$, 0.2 g/dl $(NH_4)_2SO_4$, 0.1 g/dl sodium citrate, 0.02 g/dl $MgSO_4.7H_2O$, and 0.5 g/dl glucose, and cultured at 37° C. After 3 days cultivation, 3 colonies appeared on the agar medium, and were picked up to purify. The three transformants obtained were tryptophan prototroph and resistant to 5-fluorotryptophan, and all of the three transformants produced extracellular tryptophan.

Among the three transformants, AJ 11714 (FERM-BP 209) which had highest productivity of L-tryptophan was selected. DNAs in AJ 11714 was extracted from it by C. I. Kado's phenol method (J. Bac., 145, 3, 1365 (1981)).

Plasmid DNA and chromosomal DNA were separated by agarose-gel electrophoresis, and plasmid DNA obtained was purified by dialysis.

The purified plasmid was incorporated into AJ 11713, which produces L-tryptophan, by the manner shown in step (3), and as the desired transformant, kanamycin and 5-fluorotryptophan-resistant AJ 11715 (FERM-BP 210) was obtained.

(5) Tryptophan production by the new tryptophan producers

L-tryptophan productivity of AJ 11713, AJ 11714 and AJ 11715 were tested as follows.

Twenty ml batches of a culture medium at pH 7.0, which contained, per deciliter, 8 g glucose, 1 g $NH_4Cl$, 0.2 g KCl, 0.1 g $KH_2PO_4$, 0.04 g $MgSO_4.7H_2O$, 0.4 g "casamino acid", 1 mg $FeSO_4.4H_2O$, 1 mg $MnSO_4.4H_2O$, 20 mg L-arginine, 20 mg L-leucine and 4 g $CaCO_3$, were placed in 500 ml-shaking flasks. Five μg/ml kanamycin was added further to the medium for AJ 11714 and AJ 11715.

Cultivation was carried out at 30° C. for 96 hours with shaking. After 48 hours of the cultivation, anthranilic acid was added to one batch of the medium to contain 0.5 g/dl. Small amounts of indole were fed to another one batch of the medium from 48 hours to 96 hours, and total amounts of indole fed became 0.5 g/dl.

The amounts of L-tryptophan in the supernatant of the resulting culture media were determined by microbiological-assay, and are shown in Table 1.

TABLE 1

| Microorganism tested | L-Tryptophan accumulated (mg/dl) Additive | | |
|---|---|---|---|
| | Anthranilic acid | Indole | None |
| AJ 11713 | 110 | 120 | 20 |
| AJ 11714 | 140 | 155 | 70 |
| AJ 11715 | 230 | 310 | 80 |

AJ 11712 can be easily obtained by removing plasmid from AJ 11714 by a conventional manner as mentioned below: AJ 11714 is cultured with shaking in 4 ml of CMG-2 medium at pH 7.0 containing 0.5 g/dl glucose, 1 g/dl yeast extract, 1 g/dl peptone and 0.5 g/dl NaCl and placed in 20 ml-test tube. The temperature is adjusted to 30° C. from initiation to 12 hours, and 41° C. from 12 hours to 36 hours. Cells in the resulting culture broth are collected, suspended in sterilized water, and spread on a CMG-2-agar-plate. The plate is then incubated at 30° C. for one day, and is replicated onto the second CMG-2-agar-plate containing 10 μg/ml kanamycin. The second CMG-2-agar-plate is incubated at 30° C. for 1 day. The strain which cannot grow on the second CMG-2-agar-plate is separated as AJ 11712.

What is claimed is:

1. A method for producing L-tryptophan by fermentation which comprises:

(a) aerobically culturing an L-tryptophan-producing microorganism having the identifying characteristics of *Bacillus subtilis* AJ 11715 in an aqueous culture medium containing a carbon source and a nitrogen source in the absence of anthranilate and indole; and (b) recovering the L-tryptophan accumulated in the culture medium.

2. A method for producing L-tryptophan by fermentation which comprises:

(a) aerobically culturing an L-tryptophan-producing microorganism having the identifying characteristics of *Bacillus subtilis* AJ 11714 in an aqueous culture medium containing a carbon source and a nitrogen source in the absence of anthronilate and indole; and (b) recovering the L-tryptophan accumulated in the culture medium.

* * * * *